United States Patent
Layer

[11] 4,301,306
[45] Nov. 17, 1981

[54] NORBORNENYL PHENOLIC COMPOUNDS
[75] Inventor: Robert W. Layer, Cuyahoga Falls, Ohio
[73] Assignee: The B. F. Goodrich Company, Akron, Ohio
[21] Appl. No.: 134,380
[22] Filed: Mar. 27, 1980
[51] Int. Cl.³ .............................................. C07C 39/23
[52] U.S. Cl. ................................. 568/734; 568/732; 568/719
[58] Field of Search ................ 568/719, 734, 721, 732
[56] References Cited
U.S. PATENT DOCUMENTS 2,537,636  1/1951  Kitchen .............................. 568/734
4,067,899  1/1978  Mardiguian ........................ 568/734
4,112,000  9/1978  Mardiguian ........................ 568/734

Primary Examiner—Werren B. Lone
Attorney, Agent, or Firm—George A. Kap; J. Hughes Powell, Jr.

[57] ABSTRACT

Novel norbornenyl phenolics useful as antioxidants are defined by the following structural formula:

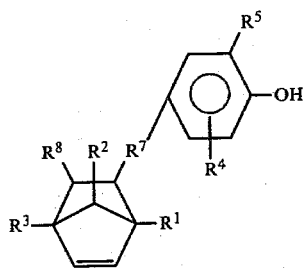

where $R^1$, $R^2$, and $R^3$ are individually selected from hydrogen and alkyl groups of 1 to 3 carbon atoms; $R^4$ is selected from hydrogen, alkyl groups containing 1 to 12 carbon atoms, and substituted and unsubstituted alicyclic groups of 4 to 8 carbon atoms; $R^5$ is selected from alkyl groups containing 1 to 6 carbon atoms, and substituted and unsubstituted alicyclic groups of 4 to 8 carbon atoms; $R^7$ is selected from alkylene and alkenylene groups containing 1 to 8 carbon atoms; and $R^8$ is selected from hydrogen, alkyl and alkenyl groups containing 1 to 8 carbon atoms.

5 Claims, No Drawings

NORBORNENYL PHENOLIC COMPOUNDS

BACKGROUND OF THE INVENTION

Cyclopentadiene is present to the extent of about 15% in the naphtha cracker $C_5$ by-products stream from ethylene plants. One way to dispose of the $C_5$ by-products stream is to use it as a fuel stock; a better use is as a source of petrochemicals. The most sought-after component of the $C_5$ by-products stream is isoprene, which is also present at about 15% level. With the soaring price of natural rubber, pressure is mounting to expand synthetic polyisoprene production. For every pound of extract isoprene capacity that comes on stream, there will be a pound of cyclopentadiene. Thus, it stands to reason that with the sharp rise in the cost of crude oil, ethylene producers will have a strong incentive to find the most profitable uses for the by-products. In this context, cyclopentadiene is high on the list since its removal from the $C_5$ stream is easily accomplished at the first step of the $C_5$ purification process.

It is, therefore, desirable to promote reactions involving cyclopentadiene and derivatives thereof to produce useful products.

SUMMARY OF THE INVENTION

This invention relates to novel norbornenyl phenolics which are prepared by reacting substituted or unsubstituted cyclopentadiene with phenolic compounds at elevated temperature to produce reaction products which have antioxidant activity.

DETAILED DESCRIPTION OF THE INVENTION

Cyclopentadienes that can be reacted with phenolic compounds have the following structure:

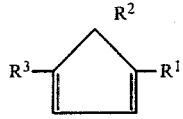

where $R^1$, $R^2$ and $R^3$ are independently selected from hydrogen and alkyl radicals of 1 to 3 carbon atoms, preferably, $R^1$, $R^2$ and $R^3$ are individually selected from hydrogen and methyl groups.

Suitable phenolic compounds that can be reacted with cyclopentadiene include those represented by the following structural formula:

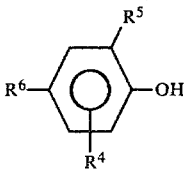

where $R^4$ is hydrogen, an alkyl group of 1 to 12 carbon atoms, or a substituted or unsubstituted alicyclic group of 4 to 8 carbon atoms, preferably $R^4$ is an alkyl group of 1 to 6 carbon atoms positioned at the open ortho position; $R^5$ is an alkyl group of 1 to 12 carbon atoms or a substituted or unsubstituted alicyclic group of 4 to 8 carbon atoms, preferably $R^5$ is an alkyl group of 1 to 6 carbon atoms; and $R^6$ is an alkenyl group of 2 to 12 carbon atoms, preferably 3 to 6, containing one unsaturated bond, preferably positioned terminally. These phenolic compounds are prepared by reacting an alkylene halide with a substituted phenol in order to introduce the unsaturated group onto the phenyl ring. In a subsequent reaction with cyclopentadiene, the unsaturated group makes possible the formation of the norbornenyl phenolic. The reaction between an alkylene halide and a substituted phenol is carried out under a blanket of nitrogen in the presence of a solvent, such as dimethyl formamide or dimethyl sulfoxide, and an alkali metal alkoxide catalyst, such as sodium methoxide.

Specific examples of alkylene halides include allyl halide such as allyl bromide; allyl chloride; 6-chloro-1-hexene; 4-bromo-1-octene, and others, all of which can contain lower alkyl substituents on the carbon chains. Suitable examples of substituted phenols which can be used in the reaction with alkylene halides to produce phenolic compounds include 2,6-di-t-butylphenol, 2-t-butyl-5 methylphenol, 2-octyl-6-t-butylphenol, 2-t-butyl-6-cyclohexylphenol, 2-hexyl-6-cyclohexylphenol, and 2-t-pentyl-6-methylcyclohexylphenols.

The reaction between a phenolic compound and cyclopentadiene is exemplified below by means of the following equation:

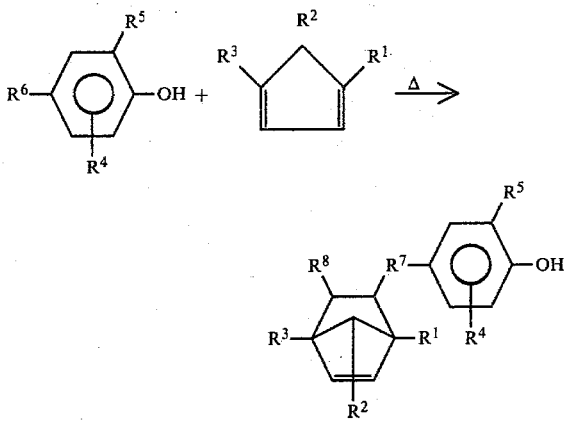

where $R^1$, $R^2$, $R^3$, $R^4$, $R^5$, and $R^6$ are as previously defined; $R^7$ is selected from alkylene and alkenylene groups containing 1 to 8, preferably 1 to 4 carbon atoms; and $R^8$ is selected from hydrogen, and alkyl and alkenyl groups of 1 to 8, preferably alkyl groups of 1 to 4 carbon atoms.

The norbornenyl phenolics of this invention provide antioxidant function in various materials, such as synthetic natural rubber, styrene-acrylonitrile rubber and other thermoplastics and elastomers. These novel compounds can be bound into a polymer backbone by various polymerization techniques and thus provide a number of significant advantages which are characterized by the fact that such antioxidants are not lost as a result of leaching or volatilization and they are not redistributed, which means that blooming is eliminated.

This invention will now be illustrated by a number of specific examples which are presented for the purpose of elucidating the disclosure of the invention claimed herein. These examples are not to be construed as limiting in any way the scope of the appended claims.

EXAMPLE 1

This example illustrates preparation of a phenolic compound which is subsequently reacted with cyclopentadiene to form a novel norbornenyl phenolic. The reactants are di-t-butylphenol and allyl bromide and the product is 4-allyl-2,6-di-t-butylphenol.

The reaction was carried out by charging a one liter, 3-necked reactor with 11.8 g (0.218 mole) sodium methoxide and 200 ml of dry dimethyl formamide. The suspension was stirred at room temperature. A solution of 41.2 g (0.200 mole) of the substituted phenol in 100 ml of dry dimethyl formamide was then added to the reactor and the contents thereof were stirred for one hour. Subsequently, 25 g (0.21 mole) of allyl bromide was added over a period of 15 minutes with vigorous agitation, allowing the reaction to exotherm freely. The exotherm reached 41° C. during addition of allyl bromide but dropped soon after all of the allyl bromide was added. A sample was analyzed by vapor phase chromatography which showed 62% product formation. Then the reactor was heated and held at 50° C. for one hour and then was allowed to cool down and remain overnight at room temperature. In the morning, water was added to the reactor with stirring, followed by toluene to extract the organic matter. The toluene layer was washed with water 3 times in a large separatory funnel and then dried over sodium sulfate. The liquid was filtered off with suction and then evaporated to yield a reddish oil which was distilled under high vacuum.

EXAMPLE 2

Here, preparation of the norbornenyl phenolic is illustrated by the reaction of 4-allyl-2,6-di-t-butylphenol with cyclopentadiene, as depicted by the following equation:

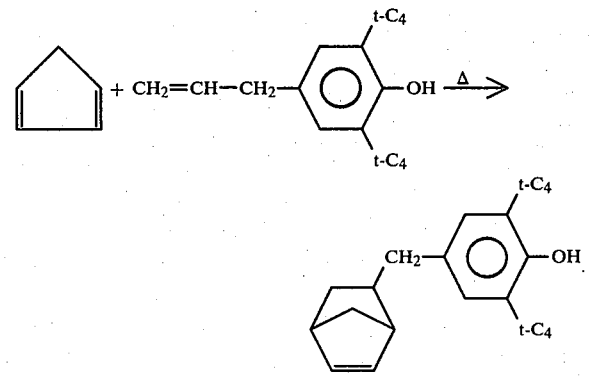

The reaction was undertaken by mixing 107 g (0.32 mole) of 4-allyl-2,6-di-t-butylphenol with 85 g (0.64 mole) of dicyclopentadiene and charging the mixture to a stainless steel high pressure reactor. Reaction temperature was maintained at about 240° C. for about 4 hours with pressure developing to about 50 psig. Under these conditions, dicyclopentadiene undergoes a retro Diels-Alder reaction to form cyclopentadiene. Samples were continuously taken for analysis. After about 4 hours of reaction time, contents of the reactor were transferred to a flask and distilled under vacuum. The product distilled at 148° to 152° C. at 1.5 mm of vacuum and was of pale yellow color. The product was identified by NMR spectroscopy. NMR (CDCl$_3$) $\delta$:1.43 (S, 18H, C—CH$_3$), 1.61–2.94 (M, 9H, C—H), 3.25 & 3.36 (D, 2H, Ar—CH$_2$), 4.99 (S, 1H, O—H), 6.96 (S, 2H, Ar—H).

EXAMPLE 3

This example demonstrates stabilizing or antioxidant properties of the norbornenyl phenolic antioxidant of Example 2 compared to butylated hydroxytoluene (BHT) antioxidant, 4-allyl-2,6-di-t-butylphenol of Example 1, and a control sample without any antioxidant additive. In each instance, 0.68 g of a given antioxidant was mixed with 68 g of reprecipitated synthetic natural rubber, i.e., polyisoprene, in a Brabender Plasticorder for two minutes at 80° C. No antioxidant was added to the control sample, it consisted only of SN rubber. Each sample was prepared and tested for Mooney viscosity before and after aging pursuant to ASTM D-1646-72 test using a large rotor and 1-minute warm-up time. Mooney buttons were aged at 70° for 10 days in an oven, as prescribed by ASTM D-573-67 test. Table I, below, symmarizes results of these tests.

TABLE I

| Antioxidant | Mooney Viscosity After No Aging | | | Mooney Viscosity After 10 Days at 70° C. | | | % Retained Viscosity on 10-Min. Values |
| --- | --- | --- | --- | --- | --- | --- | --- |
| | Immediate | 4-Min. Shearing Time | 10-Min. Shearing Time | Immediate | 4-Min. Shearing Time | 10-Min. Shearing Time | |
| BHT | 76 | 59 | 56 | 60 | 47 | 45 | 80 |
| Norbornenyl Phenolic of Example 2 | 80 | 59 | 54 | 58 | 44 | 40 | 74 |
| Allyl Compound of Example 1 | 76 | 58 | 55 | 49 | 37 | 34 | 62 |
| None | 76 | 55 | 54 | <10 | <10 | <10 | <20 |

Results in the above table indicate viscosity retention of 74% for the norbornenyl phenolic antioxidant versus 80% for BHT, a commonly used antioxidant for synthetic rubbers and plastics. This reflects that norbornenyl phenolic antioxidant retains the physical properties after aging nearly as well as BHT. The norbornenyl phenolic antioxidant performs as well or better than other commercial antioxidants in terms of maintaining physical properties of polymers on aging. In service, BHT is known to suffer from the severe disadvantage of volatilization and extraction from the polymers. On the other hand, norbornenyl phenolic antioxidants, which contain a uniquely reactive double bond in the norbornenyl moiety, can be polymerized into the backbone of the polymer and thus become immune to volatization and extraction losses.

I claim:

1. Novel compounds defined by the following structural formula:

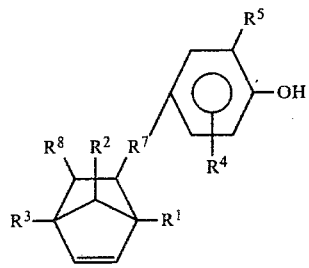

where $R^1$, $R^2$, and $R^3$ are individually selected from hydrogen and alkyl groups of 1 to 3 carbon atoms; $R^4$ is selected from hydrogen, alkyl groups containing 1 to 12 carbon atoms, and substituted and unsubstituted alicyclic groups of 4 to 8 carbon atoms; $R^5$ is selected from alkyl groups containing 1 to 6 carbon atoms, and substituted and unsubstituted alicyclic groups of 4 to 8 carbon atoms; $R^7$ is selected from alkylene and alkenylene groups containing 1 to 8 carbon atoms; and $R^8$ is selected from hydrogen and alkyl and alkenyl groups containing 1 to 8 carbon atoms.

2. Compounds of claim 1 wherein $R^1$, $R^2$, and $R^3$ are individually selected from hydrogen; $R^4$ and $R^5$ are individually selected from alkyl groups of 1 to 6 carbon atoms; $R^7$ is selected from alkylene groups containing 1 to 4 carbon atoms; and $R^8$ is selected from alkyl groups containing 1 to 4 carbon atoms.

3. Compounds of claims 2 wherein $R^4$ and $R^5$ are selected from t-alkyl groups of 4 to 6 carbon atoms.

4. Compounds of claim 2 wherein $R^1$, $R^2$, and $R^3$ are hydrogens, both $R^4$ and $R^5$ are t-butyl groups, $R^7$ is a methylene group, and $R^8$ is hydrogen.

5. Compounds of claim 4 wherein $R^4$ group is located on the open ortho position relative to the hydroxyl group.

* * * * *